(12) United States Patent
Mahnken et al.

(10) Patent No.: US 8,750,589 B2
(45) Date of Patent: Jun. 10, 2014

(54) METHOD FOR GENERATING A TOMOGRAPHIC TEMPERATURE MAP IN A PATIENT BY WAY OF A CT DEVICE, CONTROL AND COMPUTING UNIT AND CT SYSTEM

(75) Inventors: Andreas Mahnken, Aachen (DE); Bernhard Schmidt, Fürth (DE)

(73) Assignee: Siemens Aktiengesellschaft, Munich (DE)

( * ) Notice: Subject to any disclaimer, the term of this patent is extended or adjusted under 35 U.S.C. 154(b) by 193 days.

(21) Appl. No.: 13/271,285

(22) Filed: Oct. 12, 2011

(65) Prior Publication Data

US 2012/0093382 A1 Apr. 19, 2012

(30) Foreign Application Priority Data

Oct. 13, 2010 (DE) .......................... 10 2010 042 385

(51) Int. Cl.
*G06K 9/00* (2006.01)
(52) U.S. Cl.
USPC .......................................................... 382/131
(58) Field of Classification Search
None
See application file for complete search history.

(56) References Cited

U.S. PATENT DOCUMENTS 4,889,122 A * 12/1989 Watmough et al. ............... 601/3
2004/0223585 A1 * 11/2004 Heismann et al. .............. 378/54

2008/0273666 A1 * 11/2008 Walter et al. .................. 378/185
2009/0052610 A1    2/2009 Denham
2010/0185087 A1    7/2010 Gustafson

FOREIGN PATENT DOCUMENTS

| DE | 10143131 A1 | 4/2003 |
|---|---|---|
| DE | 102008049604 A1 | 4/2010 |
| DE | 102009036027 A1 | 12/2010 |

OTHER PUBLICATIONS

Sandison, George A., et al. "X-ray CT monitoring of iceball growth and thermal distribution during cryosurgery." Physics in medicine and biology 43.11 (1998): 3309.*
German Priority Application No. 10 2010 042 385.8 dated Oct. 13, 2010 (not yet published).

* cited by examiner

*Primary Examiner* — Stephen R Koziol
*Assistant Examiner* — Amandeep Saini
(74) *Attorney, Agent, or Firm* — Harness, Dickey & Pierce, P.L.C.

(57) ABSTRACT

A method for generating a tomographic temperature map in a patient by use of a CT device, a computing unit and CT system with computing unit are disclosed. In at least one embodiment of the method, the local distribution of density and mean atomic number is determined on the basis of tomographic image data from different X-ray energy regions, and a local temperature distribution in the tissue of the patient is ascertained from previously experimentally determined or theoretically calculated relations between Z values, density and temperature.

17 Claims, 4 Drawing Sheets

METHOD FOR GENERATING A TOMOGRAPHIC TEMPERATURE MAP IN A PATIENT BY WAY OF A CT DEVICE, CONTROL AND COMPUTING UNIT AND CT SYSTEM

PRIORITY STATEMENT

The present application hereby claims priority under 35 U.S.C. §119 on German patent application number DE 10 2010 042 385.8 filed Oct. 13, 2010, the entire contents of which are hereby incorporated herein by reference.

FIELD

At least one embodiment of the invention generally relates to a method for generating a tomographic temperature map in a patient by way of a CT device. More specifically, it relates to a method wherein a temperature distribution is inferred based on a measured density distribution obtained by way of a rho/Z decomposition of tomographic image data acquired on the basis of different X-ray energies and the temperature distribution is visualized as an image. At least one embodiment of the invention also generally relates to a computing unit with storage medium in which computer programs or program modules are stored which perform the cited method during operation, and/or to a CT system having such a computing unit.

BACKGROUND

A method for determining a temperature or temperature distribution in an object region having a composition consisting of n different material components is known from the disclosure of the publication DE 10 2008 049 604 A1, wherein:

- an X-ray computed tomography system is used, by way of which image data sets can be recorded at different spectral distributions of X-ray radiation,
- image data sets of the object region are recorded at n different spectral distributions of the X-ray radiation by way of the computed tomography system,
- densities, attenuation values or CT values for the n different material components which have a known dependence on the temperature as well as possibly on the location in the object region are determined from the image data sets by material decomposition, and
- the temperature at one or more points of the object region is ascertained on the basis of the determined densities, attenuation values or CT values as well as of the known dependence of at least one of the variables on the temperature and possibly on the location.

According to the known method, an X-ray computed tomography system is therefore used, by which image data sets are recorded at different spectral distributions of the X-ray radiation. In order to ascertain the temperature or temperature distribution in an object region which is composed of n different material components, the computed tomography system is used to record n image data sets of the object region at n different spectral distributions of the X-ray radiation. From the n image data sets the densities, attenuation values or CT values for the n different material components are then determined by way of the known material decomposition technique. The temperature at one or more points of the object region is then ascertained on the basis of the determined densities, attenuation values or CT values as well as of the known dependence of said variables on the temperature. In this case the dependence of the density of the respective material on the temperature can be derived from tables or determined in advance by means of measurements.

SUMMARY

The inventors have recognized that, in practice however, it has been demonstrated that the measurements performed according to the known method are not yet sufficiently accurate.

In at least one embodiment of the invention, a method is disclosed for generating a tomographic temperature map in a patient with the aid of CT examinations which delivers improved accuracy.

Advantageous developments of the invention are the subject matter of subordinate claims.

The inventors have recognized that in order to ascertain a temperature change exactly it is not sufficient to relate this exclusively to the density of a multispectral CT measurement, but that a varying composition of the region studied in each case is also necessary here. Thus, in an investigated tissue region of a patient, not only can the density of said region change, due, for example, to a temperature change induced there, but in addition there is also the possibility of a change in the material composition. This can occur, for example, due to dehydration of the tissue or the formation of a liquefactive necrosis.

In accordance with at least one embodiment, the inventors in at least one embodiment propose a method for generating a tomographic temperature map in a patient by way of a CT device which comprises the following steps of:

- sampling and tomographic reconstruction of the attenuation values of the tissue on the basis of at least two mutually different X-ray energies or X-ray energy spectra relative to at least two sets of energy-dependent image data,
- performing a rho/Z decomposition of the tomographic image data, the current local density and the current local mean Z value (Z=atomic number) being ascertained for each location,
- ascertaining a local temperature distribution in the tissue, the current local temperature values being determined from previously experimentally determined or theoretically calculated relations between Z values, density and temperature, and
- outputting and/or visualizing the spatial temperature distribution.

A further improvement of the method according to an embodiment of the invention can be achieved in that:

- prior to the examination it is ascertained and an assignment made for each $Z_0$ value or $Z_0$ value range which is determined under physiological conditions, how the Z values change under exposure to heat, and how a density-temperature relation is determined for said—historically stamped—$Z(Z_0)$ values, and
- the density-temperature relations which are assigned to a $Z_0$ value initially determined under physiological conditions are used for ascertaining the temperature.

Furthermore, the inventors also propose, in at least one embodiment, a computing unit with storage medium in which computer programs or program modules are stored which perform the steps of the above-described method during operation. Also, in at least one embodiment, is a CT system which includes such a computing unit.

BRIEF DESCRIPTION OF THE DRAWINGS

The invention is described in more detail below with reference to the example embodiments and the figures, only those features necessary to an understanding of the invention being presented. The following reference signs are used: 1: dual-energy CT system/C-arm system; 2: first X-ray tube; 3: first detector; 4: second X-ray tube; 5: second detector; 6: gantry housing/drive system; 7: C-arm; 8: patient couch; 9: system axis; 10: open- and closed-loop control unit; M1-M3: tissue regions; P: patient; $Prg_1$ to $Prg_n$: computer programs; T: tissue temperature; Z: atomic number; I-V: phases in the tissue change.

Specifically in the figures.

DETAILED DESCRIPTION OF THE EXAMPLE EMBODIMENTS

Figure 1:
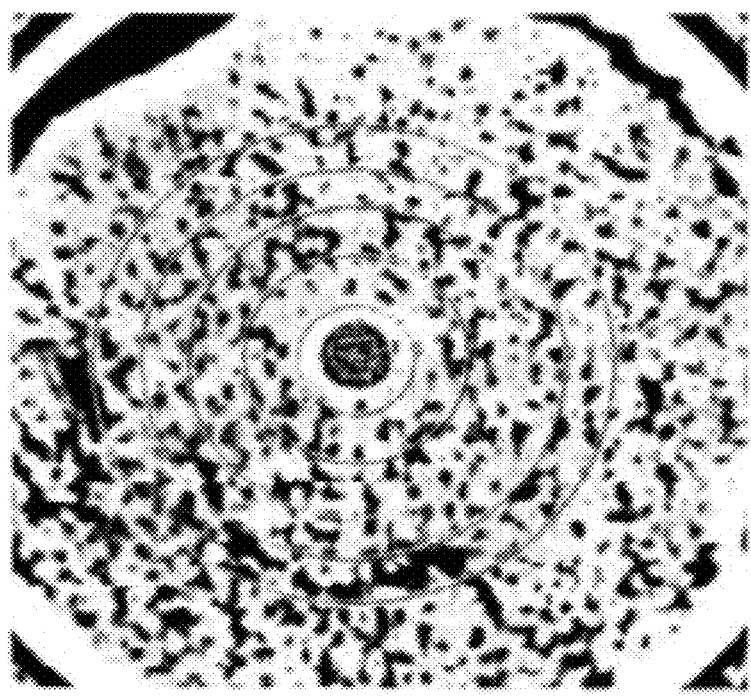
FIG. 1: shows a sectional image (slice) through a tissue region in the physiological state.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Figure 2:
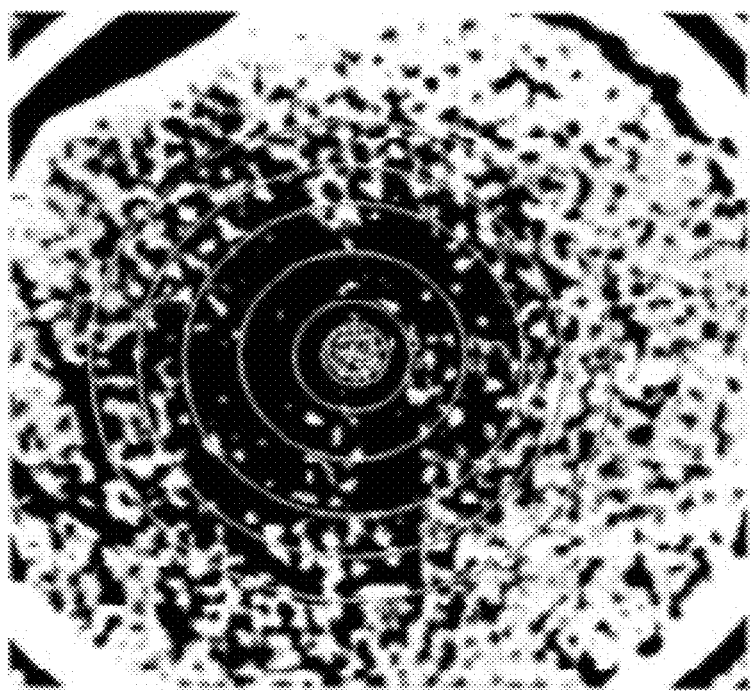
FIG. 2: shows a sectional image according to FIG. 1, with partially heated tissue.

FIGS. 1 and 2 show an identical tomographic section through a tissue, physiological conditions at 37° C. prevailing in the tissue in FIG. 1. The black-and-white drawings shown with predominantly light spots show the investigated tissue with its typical density distribution at approx. 37° C. The locally identical sectional image in FIG. 2 shows a situation with a temperature increase in the central section, initially no significant substantial change of the tissue—i.e. no change in the mean Z value—having taken place here initially. Owing to the temperature increase a reduction in the density of the tissue results, this being reflected in a reduced absorption of the X-ray radiation and consequently an increase in dark regions being generated. If a further temperature increase takes place, this leads to chemical and physical processes which also cause a change in the mean Z value as a function of the temperature but also of the investigated material.

Figure 3:
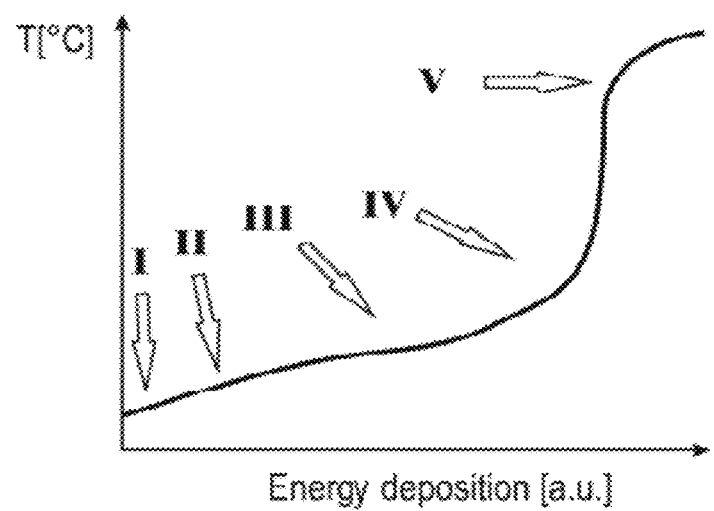
FIG. 3: shows an exemplary curve of a temperature change in the tissue for energy deposition.

The progressive curve of such a temperature change is shown in FIG. 3. In this case the specific energy deposition in the tissue is plotted on the abscissa versus the tissue temperature T reached as a result on the ordinate. The different phases of the tissue change with a physiological starting temperature of 37° C. are designated by the Roman numerals I to V.

Initially a heating of the tissue takes place at I. As the temperature increases this heating leads to coagulation of the tissue in the area II with a subsequent desiccation phase III. This is followed by carbonization in the area IV and finally, with continuing energy deposition and temperature increase associated therewith, to vaporization in the area V.

Since every tissue type and also every tissue volume has a different composition and at the same time specifying a mean atomic number Z is also not sufficient to unequivocally ascertain the actual atomic composition—which ultimately is critical to the absorption behavior of an investigated voxel or region—it is advantageous to know also the "historical" development of a voxel or range of multiple voxels and to know, on the basis of the mean Z value at a time instant with physiological conditions, its known—possibly from preliminary experiments—dependence on a density $\rho$ varying due to temperature increase. With the aid of these functions and known physiological $Z_0$ value it is then possible—likewise based on corresponding preliminary experiments or calculations—also to ascertain the actual temperature precisely on the basis of the determined density value following a rho/T decomposition.

With regard to the problem of the absence of unambiguousness of the mean Z value it is pointed out for example that the mean Z value of both Cl—H (hydrogen chloride) and F (fluorine) is 9, even though these are substances exhibiting different absorption behaviors. This also applies analogously in the case of more complex organic compounds and mixtures in the tissue.

Figure 4:
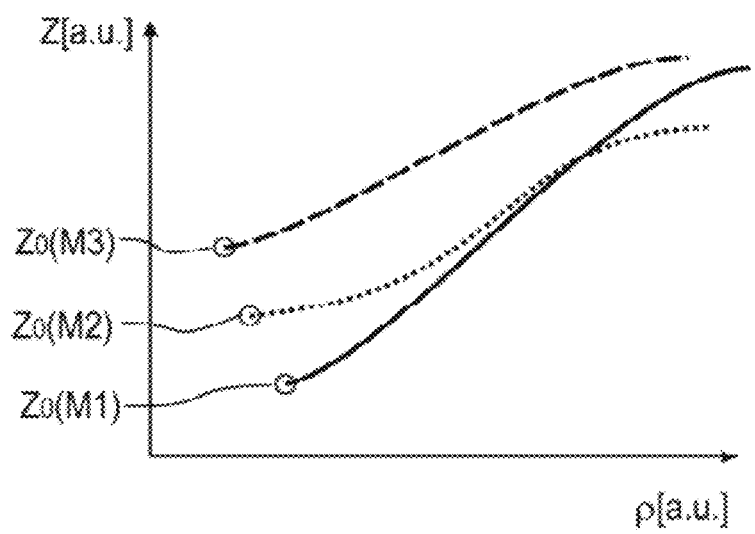
FIG. 4: shows a schematic representation of the dependence of the mean Z value on the temperature of different tissue compositions M1 to M3.

FIG. 4 shows in a purely schematic representation the behavior of different materials or tissue regions M1 to M3 which are heated by input of energy and the curve of the change in the mean Z value plotted over the changing density. The starting points (circled) correspond in each case to the actual density under physiological conditions and the mean Z value determined there from a rho/Z decomposition by way of at least two CT tomograms on the basis of different X-ray energy spectra.

Figure 5:
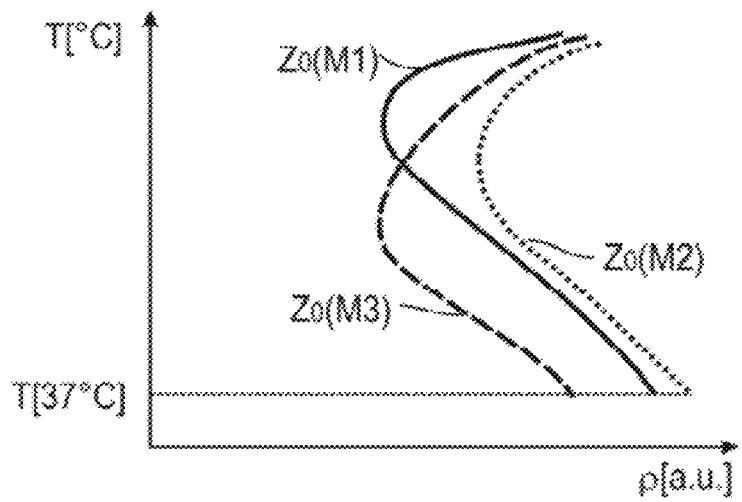
FIG. 5: shows a schematic representation of the dependence of the density of different tissue compositions on the temperature.

FIG. 5 shows in a schematic and example representation a density/temperature curve of the different materials M1 to M3 shown in FIG. 4, from which it is apparent that knowledge of a density value is not yet sufficient on its own for ascertaining the temperature of a tissue region unequivocally. Thus, if it is possible, based on the knowledge of a measurement of the mean Z value under physiological conditions, i.e. of the $Z_0$ value, to ascertain which curve in the diagram of FIG. 5 should be used as a means of orientation, the current temperature can be ascertained relatively accurately. With regard to the ambiguity of some density values that is evident from the diagram, it is possible in addition to determine the correct temperature value in each case on the basis of the curve of the density and a corresponding plausibility consideration.

If for example initial measurements taken under physiological conditions are not available, there is still also the possibility of performing an assignment to the corresponding material based on a rho/Z decomposition and the value pair of density and atomic number determined thereby in the diagram of FIG. 4.

Figure 6:
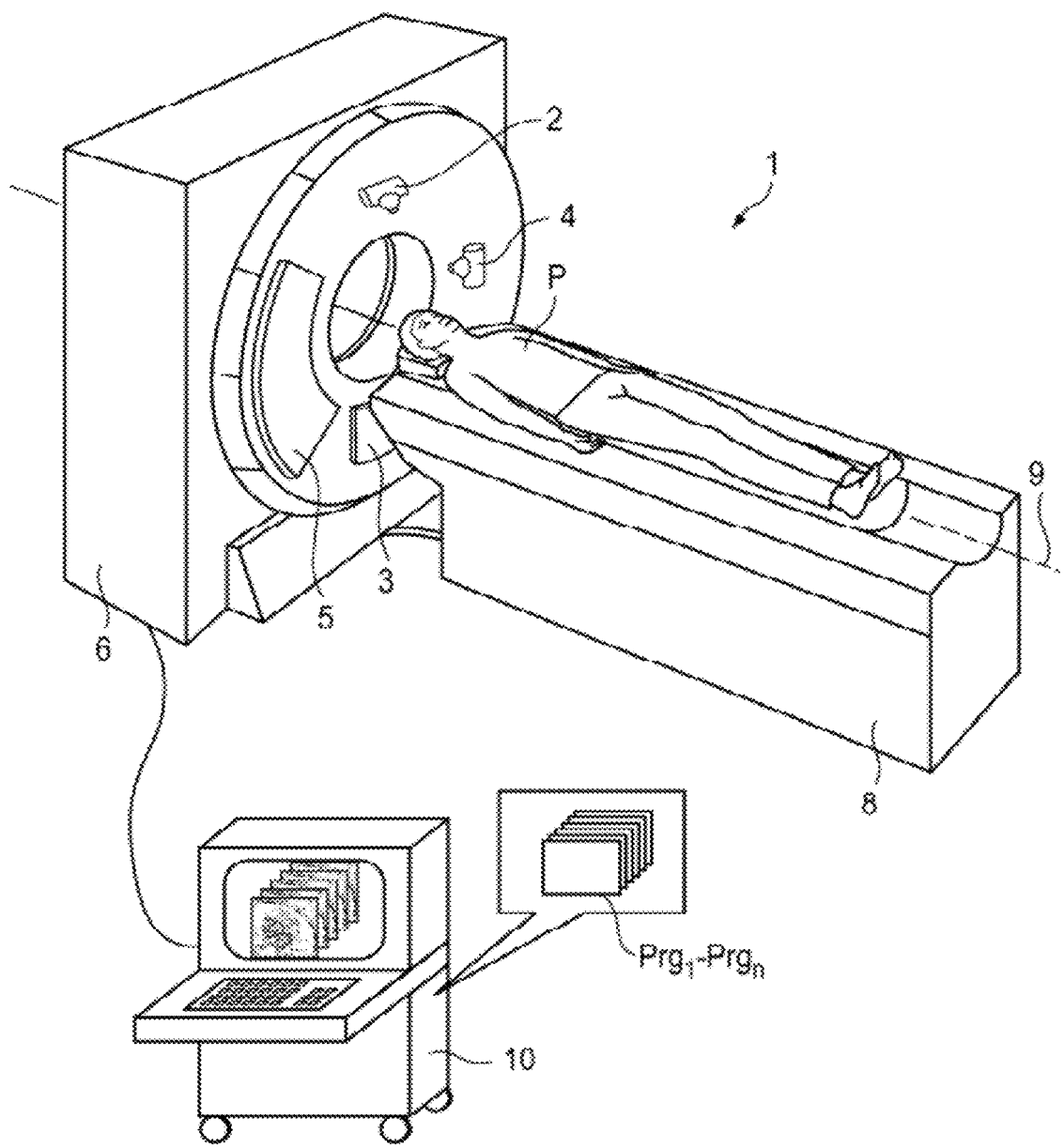
FIG. 6: shows a dual-energy CT system.

FIG. 6 shows by way of example a dual-energy CT system 1 in which the method according to an embodiment of the invention is performed. The CT system 1 includes a gantry housing 6 wherein there is mounted on the gantry a first tube/detector system, including a first X-ray tube 2 and an oppositely disposed first detector 3. A further tube/detector system can optionally be provided, like the tube/detector system depicted here, including the second X-ray tube 4 and the oppositely disposed second detector 5. During scanning the two tube/detector systems rotate around a field of view, described here by an opening in the gantry housing 6, while a patient P positioned on a movable patient couch 8 is moved through the field of view along a system axis 9. In this operation the patient P can be moved either continuously or sequentially; alternatively, if a specific region is being examined, the patient can be moved to a specific point at which he remains stationary during the scan.

The CT system 1 is controlled by way of an open- and closed-loop control unit 10 which has a memory containing computer programs $Prg_1$ to $Prg_n$ in which the necessary methods for controlling the CT system and for evaluating the received detector data, including image data corresponding to the reconstruction, are stored. The method according to an embodiment of the invention can also be coded in a computer program and be implemented in the program memory of the open- and closed-loop control unit 10, i.e. a computing unit, such that the steps of said method will be executed during the operation of the system.

Figure 7:
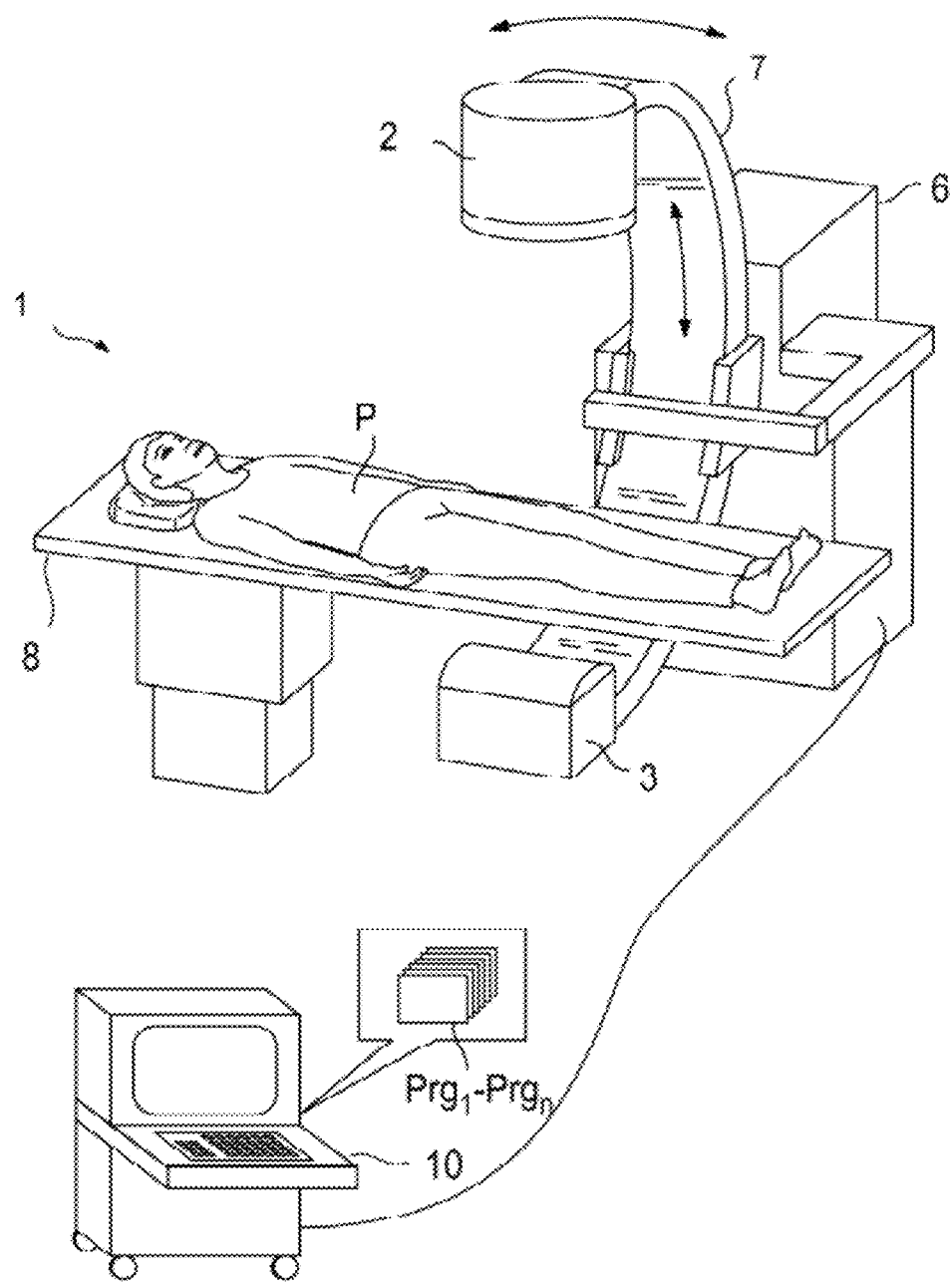
FIG. 7: shows a C-arm system.

FIG. 7 also shows a CT system in the form of a C-arm system 1 which has a C-arm 7 at the ends of which are located an X-ray tube 2 and an associated oppositely disposed detector 3. The C-arm 7 can be rotated with the aid of the drive system 6 around a patient P who is positioned on a patient couch 8. Owing to the design of the C-arm system 1 the patient P is more easily accessible during the examination.

The C-arm system 1 is adjusted and controlled by way of an open- and closed-loop control unit 10 which has computer programs $Prg_1$ to $Prg_n$, wherein here too program code can be provided in the memory of said open- and closed-loop control unit, which program code performs the method according to an embodiment of the invention during operation.

All in all, therefore, an embodiment of the present invention presents a method for generating a tomographic temperature map in a patient by way of a CT device, a computing unit and a CT system with computing unit, wherein the local distribution of density and mean atomic number is determined on the basis of tomographic image data from different X-ray energy regions, and a local temperature distribution in the tissue of the patient is ascertained from previously experimentally determined or theoretically calculated relations between Z values, density and temperature.

In accordance with at least one embodiment, the inventors in at least one embodiment propose a method for generating a tomographic temperature map in a patient by way of a CT device which comprises the following steps of:

sampling and tomographic reconstruction of the attenuation values of the tissue on the basis of at least two mutually different X-ray energies or X-ray energy spectra relative to at least two sets of energy-dependent image data, performing a rho/Z decomposition of the tomographic image data, the current local density and the current local mean Z value (Z=atomic number) being ascertained for each location, ascertaining a local temperature distribution in the tissue, the current local temperature values being determined from previously experimentally determined or theoretically calculated relations between Z values, density and temperature, and outputting and/or visualizing the spatial temperature distribution.

By way of the method the temperature is ascertained much more accurately with the aid of the density values determined by way of a CT examination.

In this case density/temperature curves or tables relating to a plurality of Z values can advantageously be used for ascertaining the temperature.

Furthermore it is also possible here to use mean Z values in which the composition of the currently investigated tissue is taken into account.

Since the rho/Z decomposition used in the method of at least one embodiment only yields a mean Z value which does not allow the actual atomic distribution of the atomic numbers to be deduced based on given tissue compositions, it can be favorable to identify which type of tissue is present at the location being investigated and, according to the tissue type, to use density/temperature curves or density/temperature value tables assigned thereto for ascertaining the temperature. Thus, mean Z values are used in the composition of which the currently investigated tissue with its actual atomic composition is taken into account.

A further improvement of the method according to an embodiment of the invention can be achieved in that:

prior to the examination it is ascertained and an assignment made for each $Z_0$ value or $Z_0$ value range which is determined under physiological conditions, how the Z values change under exposure to heat, and how a density-temperature relation is determined for said—historically stamped—$Z(Z_0)$ values, and the density-temperature relations which are assigned to a $Z_0$ value initially determined under physiological conditions are used for ascertaining the temperature.

In this embodiment variant of the method it is therefore taken into account which behavior a particular tissue, characterized by its mean Z value under physiological conditions, i.e. at approximately 37° Celsius and in the non-denatured state, exhibits in the case of a temperature rise on the one hand in relation to its change in the mean Z value and on the other hand also how the density-temperature relation behaves in the case of the respective material. By this, therefore, the actual composition of the tissue and its individual change due to heating are taken more precisely into account. In addition the type of heating and the time characteristic of the heating can also be taken into account in order to be able to ascertain yet more accurate temperature values.

The above-described method in respect of the tomographic image data can advantageously be applied to sectional image data sets or also volume image data sets.

It is also especially favorable, in particular when the temperature distribution is to be ascertained over a relatively long period of time, if the different sets of tomographic image data acquired in multiple iterations of the method are registered on top of one another. By this, small displacements of the observed tissue due to a movement of the patient between the image acquisitions can be compensated for.

Finally the determined temperature distribution, that is to say a temperature map, can be overlaid with tomographic image data registered thereon. For example, the temperature of the tissue can be represented therein by means of differently weighted color contrast or by different colors which can be superimposed on the CT image that is present per se in black and white.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

It is to be understood that the features of embodiments of the invention which have been cited hereintofore can be used not only in the combination disclosed in each case, but also in other combinations or in isolation, without departing from the scope of the invention.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for generating a tomographic temperature map in a patient using a CT device, the method comprising:
   sampling and tomographically reconstructing attenuation values of tissue based on at least two mutually different X-ray energies or X-ray energy spectra relative to at least two sets of energy-dependent image data to generate tomographic image data;
   performing a rho/Z decomposition of the tomographic image data, and ascertaining a current local density and a current local mean Z value for each location;
   ascertaining a local temperature distribution in the tissue, current local temperature values being determined from previously experimentally determined or calculated relations between Z values, density and temperature; and
   at least one of outputting and visualizing a spatial temperature distribution based on the ascertaining.

2. The method as claimed in claim 1, wherein for a plurality of Z values, density and temperature curves or density and temperature tables are used in order to ascertain the temperature.

3. The method as claimed in claim 1, wherein mean Z values are used in which the composition of the currently investigated tissue is taken into account.

4. The method as claimed in claim 1, further comprising:
   determining how the Z values change during heating, and density-temperature relations assigned to a $Z_0$ value initially determined under physiological conditions are used for ascertaining the temperature.

5. The method as claimed in claim 1, wherein sectional image data sets are used as tomographic image data.

6. The method as claimed in claim 1, wherein volume image data sets are used as tomographic image data.

7. The method as claimed in claim 1, wherein the sets of tomographic image data acquired in multiple iterations of the method are registered on top of one another.

8. The method as claimed in claim 1, wherein the determined temperature map is overlaid with tomographic image data registered thereon.

9. A computing unit including a non-transitory computer readable storage medium in which computer programs or program modules are stored, the computing unit being configured to perform, during operation, at least the following:
   sampling and tomographically reconstructing attenuation values of tissue based on at least two mutually different X-ray energies or X-ray energy spectra relative to at least two sets of energy-dependent image data to generate tomographic image data;
   performing a rho/Z decomposition of the tomographic image data, and ascertaining a current local density and a current local mean Z value for each location;
   ascertaining a local temperature distribution in the tissue, current local temperature values being determined from previously experimentally determined or theoretically calculated relations between Z values, density and temperature; and
   at least one of outputting and visualizing a spatial temperature distribution based on the ascertaining.

10. A CT system including a computing unit as claimed in claim 9.

11. A non-transitory computer readable medium including program segments for, when executed on a computer device, causing the computer device to implement the method of claim 1.

12. The method as claimed in claim 2, wherein mean Z values are used in which the composition of the currently investigated tissue is taken into account.

13. The method as claimed in claim 2, further comprising:
    determining how the Z values change during heating, and density-temperature relations assigned to a $Z_0$ value initially determined under physiological conditions are used for ascertaining the temperature.

14. The method as claimed in claim 2, wherein sectional image data sets are used as tomographic image data.

15. The method as claimed in claim 2, wherein volume image data sets are used as tomographic image data.

16. The method as claimed in claim 2, wherein the sets of tomographic image data acquired in multiple iterations of the method are registered on top of one another.

17. The method as claimed in claim 2, wherein the determined temperature map is overlaid with tomographic image data registered thereon.

* * * * *